United States Patent
Curry et al.

(10) Patent No.: US 7,067,783 B2
(45) Date of Patent: Jun. 27, 2006

(54) METHOD FOR IMPROVED FOCUS CONTROL IN MOLECULAR ARRAY SCANNING BY USING A SYMMETRICAL FILTER TO DETERMINE IN-FOCUS-DISTANCE

(75) Inventors: Bo U. Curry, Redwood City, CA (US); Andreas N. Dorsel, Menlo Park, CA (US); Jayati Ghosh, San Jose, CA (US); Kenneth L. Staton, San Carlos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 732 days.

(21) Appl. No.: 10/261,359

(22) Filed: Sep. 30, 2002

(65) Prior Publication Data

US 2004/0061049 A1    Apr. 1, 2004

(51) Int. Cl.
*G02B 7/04* (2006.01)
(52) U.S. Cl. .................................. 250/201.3; 250/226
(58) Field of Classification Search ............. 250/201.3, 250/226
See application file for complete search history.

(56) References Cited

U.S. PATENT DOCUMENTS

| | | | |
|---|---|---|---|
| 5,091,652 A | 2/1992 | Mathies et al. | |
| 5,260,578 A | 11/1993 | Bliton et al. | |
| 5,296,700 A | 3/1994 | Kumagai | |
| 5,324,633 A | 6/1994 | Fodore t al. | |
| 5,585,639 A | 12/1996 | Dorsel et al. | |
| 5,760,951 A | 6/1998 | Dixon et al. | |
| 5,763,870 A | 6/1998 | Sadlere et al. | |
| 6,084,991 A | 7/2000 | Sampas | |
| 6,222,664 B1 | 4/2001 | Dorsel | |
| 6,284,465 B1 | 9/2001 | Wolber | |
| 6,320,196 B1 | 11/2001 | Dorsel et al. | |
| 6,335,934 B1 | 1/2002 | Sakurai et al. | |
| 6,371,370 B1 | 4/2002 | Sadler et al. | |
| 6,958,470 B1 * | 10/2005 | Hoffmann | 250/234 |

* cited by examiner

*Primary Examiner*—Que T. Le

(57) ABSTRACT

Automated methods and systems for determining an in-focus-distance for a position on the surface of a molecular array substrate using a molecular array scanner are provided. A signal from a first position of an array substrate is detected and noise is filtered out of the detected signal using a symmetrical filter to produce an in-focus-distance. In one embodiment, the in-focus-distance is utilized as an estimated in-focus-distance at a second position of the array substrate. The method finds use in maintaining the focus of a light source while scanning the array by the scanner. Also provided are methods of assaying a sample using the methods and systems of the invention, and kits for performing the invention. The subject invention finds use in a variety of different applications, including both genomics and proteomics applications.

32 Claims, 3 Drawing Sheets

METHOD FOR IMPROVED FOCUS CONTROL IN MOLECULAR ARRAY SCANNING BY USING A SYMMETRICAL FILTER TO DETERMINE IN-FOCUS-DISTANCE

FIELD OF THE INVENTION

This invention relates generally to optical scanners and, more particularly, to focus control in an array scanner.

BACKGROUND OF THE INVENTION

Array assays between surface bound binding agents or probes and target molecules in solution are used to detect the presence of particular biopolymers. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In most instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

In performing scans, a typical approach is to zigzag across an array substrate obtaining data in a raster fashion. In doing so, it has been appreciated that very slight variation in the tilt or angle of a substrate being scanned must be accounted for in order to achieve acceptable focus on successive features to accurately obtain data. As variations in substrates and scanners which cause slight variations of the tilt or angle of a substrate are extremely common, a great need exists for scanners that can automatically correct for the variation, and can effectively focus and collect data across an entire substrate without user intervention. As such, an effective and robust "autofocus" scanner would be extremely attractive.

In general, focus is achieved in an optical scanning device using a system that actuates a scanning lens assembly or the cradle carrying a sample by a servomechanism by varying the distance between these two components. The most common types of electronic feedback logic controllers for effecting automatic light source actuation and focus presently in use are the Proportional-Integral (PI) and Proportional-Integral-Derivative (PID) controllers which analyze signals from several scanned position on a substrate, make a prediction of the focal length required for correct focus of a future position, and adjust the focus of a light source accordingly. The implementation of each of these controllers varies widely and tuning and custom design of each type are well within the ability of those with ordinary skill in the art.

PI or PID autofocus controllers and the like are, in theory, capable of automatically focusing a light source during scanning of an array substrate. However, a problem with all PI, PID and related focus controllers is that high frequency (150–1000 Hz) noise arising from bearing noise, position sensing detector (PSD) noise, stray light, resonances within the control system, variations in optical path arising from scan lens motion or other sources generate instabilities in the autofocus control. As such, the noise reduce the effectiveness of the controller and prevent array substrates from being held in focus while they are being scanned. Several solutions to this problem have been investigated.

One solution to the problem is known as the "feed forward" controller, which creates a mathematical model of the slide surface, and controls the focus indirectly, by controlling the absolute position of a substrate to a setpoint derived from the model. Such an approach works best when the system being controlled is precisely known, and the external perturbations to which it is subjected can be accurately modeled. A pure feed-forward controller cannot easily cope with the variety of different substrates and differences among scanners that are commonly encountered.

Another solution is to apply either an analog or digital low-pass or bandpass asymmetric filter to the focus error signal, so as to average out the higher frequency perturbations. However, digital and analog filters that are asymmetric, i.e. those which operate using inputs from earlier time points, introduce delays and phase shifts into the filtered data, which may destabilize an autofocus control loop. Furthermore, it is known that a 250 Hz low-pass asymmetric digital filter destabilizes the autofocus controller of at least one scanner, as do similar analog filters.

A further solution is to detune the autofocus control loop (i.e. reduce the gain of the control loop) so that it does not attempt to control out high-frequency noise. However, detuning severely degrades performance. Although many adaptive control methods are available that have the ability to detune an autofocus control loop, they are either excessively computationally intensive and/or insufficiently robust. As such, they tend to be impractical.

Accordingly, a need still exists for a scanner that automatically and effectively maintains focus of a light source during scanning of an array sample. The present invention meets this, and other, needs.

Relevant Literature

U. S. patents of interest include: U.S. Pat. Nos. 5,091,652; 5,260,578; 5,296,700; 5,324,633; 5,585,639; 5,760,951; 5,763,870; 6,084,991; 6,222,664; 6,284,465; 6,371,370 6,320,196 and 6,355,934.

SUMMARY OF THE INVENTION

Automated methods and systems for determining an in-focus-distance for a position on the surface of a molecular array substrate using a molecular array scanner are provided. A signal from a first position of an array substrate is detected and high frequency noise is filtered out of the detected signal using a symmetrical filter to produce an in-focus-distance. In one embodiment, the in-focus-distance is utilized as an estimated in-focus-distance at a second position of the array substrate. The method finds use in maintaining the focus of a light source while scanning the array by the scanner. Also provided are methods of assaying a sample using the methods and systems of the invention, and kits for performing the invention. The subject invention finds use in a variety of different applications, including both genomics and proteomics applications.

DEFINITIONS

Figure 1:
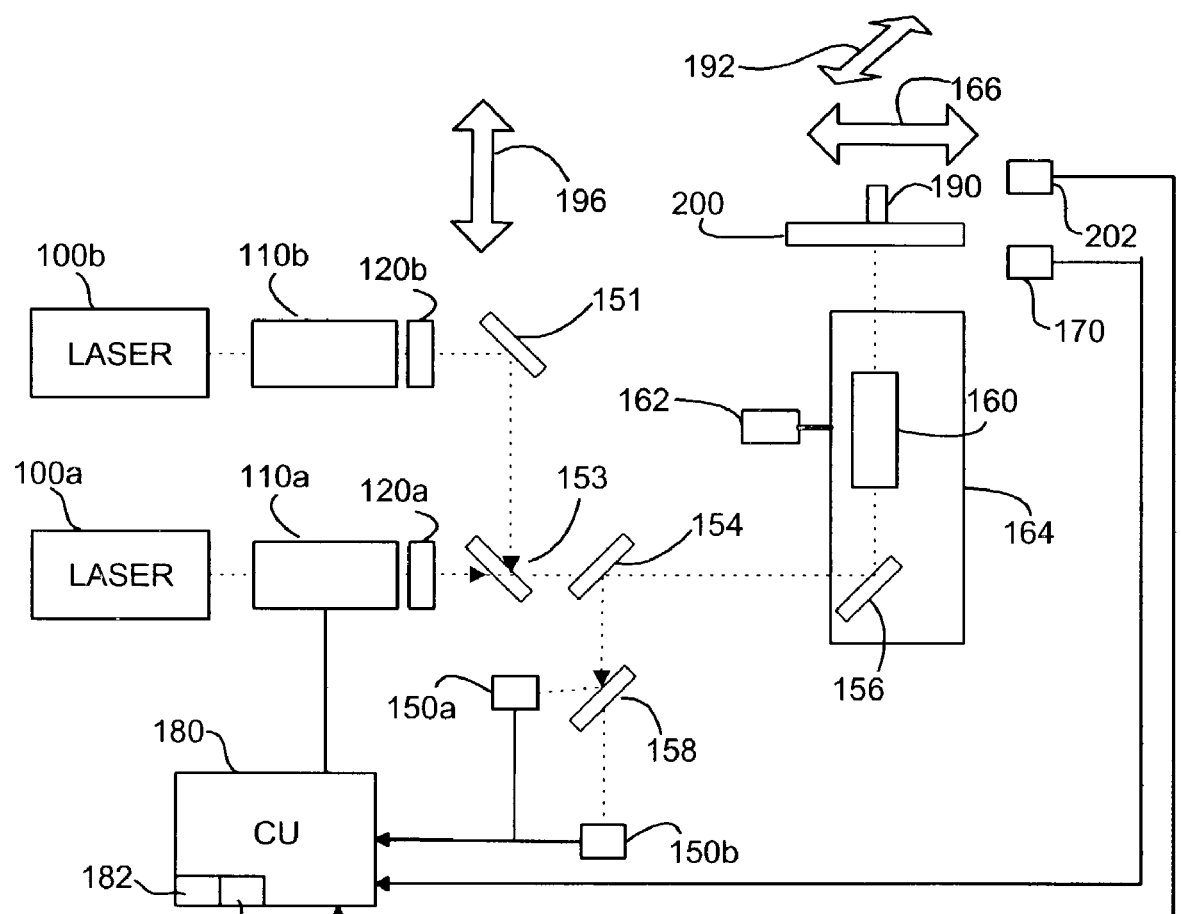
FIG. 1 schematically illustrates an apparatus as may be used in the present invention.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network).

"Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

"processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

A "scanner" is device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either confocally (employing the same lens used to focus the light onto the array) or off-axis (using a separate lens positioned to one side of the lens used to focus the onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". Biopolymer arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

The scanner typically used for the evaluation of arrays includes a scanning fluorometer. A number of different types of such devices are commercially available from different sources, such as such as Perkin-Elmer, Agilent, or Axon Instruments, etc., and examples of typical scanners are described in U.S. Pat. Nos. 5,091,652; 5,760,951, 6,320,196 and 6,355,934.

A "reference point" of a scanner autofocus system is a position of a moveable (usually in one dimension) part of the autofocus in a scanner relative to which all focus positions or distances in a scanner can be measured. In describing this invention, a scanner has a single fixed reference point. Any position within a scanner may be used as a reference point.

A "filter" is an analog or digital device which transmits a selected range of frequencies, while stopping (i.e. attenuating) others. Filters are used to suppress unwanted frequencies or noise, or to separate channels. As such, "filtering" is a process used in both analog and digital processing to pass one frequency band while blocking others or vice-versa. The "order" of a digital filter is the number of adjacent sequences of sample (sampled data of the signal-) considered in the filtering process. For example, a digital filter with an order of 10 will consider 10 adjacent sampled data of the signal in filtering a signal.

"Maintaining" correct focus or correct focus distance in relation to a substrate means the focus error signal lies within a pre-defined threshold e.g. ±0.5 µm, ±1 µm, ±2 µm or ±5 µm around the correct focus setpoint for a substrate.

DETAILED DESCRIPTION OF THE INVENTION

Automated methods and systems for determining an in-focus-distance for a position on the surface of a molecular array substrate using a molecular array scanner are provided. A signal from a first position of an array substrate is detected and high frequency noise is filtered out of the detected signal using a symmetrical filter to produce an in-focus-distance. In one embodiment, the in-focus-distance from one row of the array is utilized as an estimated in-focus-distance for the following row of the array substrate. The method finds use in maintaining the focus of a light source while scanning the array by the scanner. The current embodiment exploits the predictable periodicity of the bi-directional scanner, in which the surface of the array substrate (and therefore the required focus position) in each scan line is very nearly the same (though reversed in time) as the surface during the preceding scan line. Therefore, the observed absolute slide positions which keep the slide in focus during one scan line, provide an excellent detailed model of the positions expected to maintain focus during the subsequent scan line. This model, which we might call a "prior scan line" model, could be used to operate the controller as a "feed-forward" controller. Unfortunately, the "prior scan line" model is too detailed, since it models all the high frequency deviations as well as the desired signal. In one embodiment the high frequency noise is filtered out using either an analog or digital low-pass or band-pass filter to the above described signal. However, asymmetrical digital and analog filters (those which operate only on inputs from earlier time points), introduce delays and phase shifts into the filtered signal, which tend to destabilize the control loop if they are large enough. In the present embodiment a zero-phase filter (symmetrical filter low-pass or band-pass filter) is applied to filter out high frequency disturbances. Such a filter uses data from both before and after the filtered point, and can be designed to avoid any additional phase-shifts which are unavoidable with asymmetrical filters that use only data from before the filtered point. Design of such filters is well known in the art and is provided below. Also provided are methods of assaying a sample using the methods and systems of the invention, and kits for performing the invention. The subject invention finds use in a variety of different applications, including both genomics and proteomics applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, process or program aspects of the invention are first described. This discussion is followed by a description of suitable hardware for use in the invention and potential array use.

Methodology/Programming

The subject invention provides methods for automatically determining an in-focus-distance for a position on the surface of an array substrate. The method may be employed to automatically focus a light source and finds particular use in the scanning of an array. More specifically the methods may be employed in a sub-routine to maintain correct focus during the scanning of an array. In general, the methods involve filtering at least one signal of a scanner with a symmetrical filter. In describing the methods, the symmetrical filter used in the invention will be described first, followed by methods of using the symmetrical filter to automatically focus a light source.

Symmetrical Filters

A symmetrical filter is employed to filter a signal generated by a detector of the scanner. Symmetrical filters are well described in the filter arts (e.g. Karl, J. H., 1989, An introduction to digital signal processing, Academic Press, Inc., San Diego, Calif. 92101), however a general description of a symmetrical filter is given below.

In general terms, a symmetrical filter is a filter that considers an equal number of adjacent signal samples taken of the signal on each side of a signal sample to be filtered. The number of adjacent signal samples is referred to as the "order" of the filter, and can be described by the formula $2k+1$, where k is the number of signal samples before and after the signal sample to be filtered. For example, a symmetrical filter with an order of 21 ($=2k+1$) will sample 21 signals, including 10 ($=k$) on either side of the sample to be filtered. In a symmetrical digital filter, the considered signal samples are generally arranged in pairs that are equidistant from the sample to be filtered, e.g. for a 21st order filter if the signal sample to be filtered is the $11^{th}$ data point, and samples 10 and 12 are equidistant from the $11^{th}$, as are samples 9 and 13, and so on. As such, signal samples considered by a symmetrical digital filter are arranged in pairs, each member of the pair being equidistant from the signal to be filtered. A symmetrical filter may be, for example, a simple moving average filter, a binomial filter or Gaussian filter (Mitchell et al 1966, Climatic change, Technical Note 79: Geneva, World Meteorological Organization), or a windowed method Hamming window (Karl, J. H., 1989, An introduction to digital signal processing, Academic Press, Inc., San Diego, Calif. 92101). In the context of a scanner, a symmetrical filter order refers to a number of signals from positions that are adjacent on a scan line, i.e. the line generated by optical illumination while scanning a sample substrate. As such, since a line is generated by movement of a light source in relation to sample substrate, a symmetrical filter will consider an equal number of signal samples before (in time) and after (in time) a signal to be filtered. A symmetrical filter is a type of "zero phase" filter, where a zero phase filter samples symmetrically around a position. A zero-phase filter does not introduce any additional phase delays to the filtered sequence.

In one embodiment, the order of the symmetrical filter used is 21, however any symmetrical filter of the order $2k+1$, where k is any integer, may be used. As such, filters of the order of 3, 5, 9, 15, up to 25, up to 31, up to 51, up to 71, up to 101 or up to 501 or up to 1001 or more may be used. Generally the first k sample points and the last k sample points for which k adjacent points are not available on one of the sides (either before or after) in an equally long previous scan line, the unfiltered data may used as estimated positions for those 2k points.

The symmetrical filter utilized in the invention may be used to filter out high frequency of usually about 150 Hz to about 1000 Hz, more usually about 300 Hz to about 900 Hz, and normally about 500 Hz to about 800 Hz. In many embodiments, the symmetrical filter is used to filter out high frequency noise above a frequency of about 150 Hz, 300 Hz, 500 Hz, 700 Hz 1000 Hz or even 1500 Hz. Suitable filters include digital low-pass and band pass filters.

Methods of Determining In-Focus-Distance

An unfiltered processed component signal from an absolute distance or focus error measuring device alone is not accurate enough to determine an in-focus-distance because of unwanted noise that are found in the signals. In the methods of the invention, a symmetrical filter removes unwanted noise from the component signal, allowing an accurate determination of the in-focus-distance.

With respect to focus, "in focus" or "correct focus" means that a position on a substrate is distanced from a focused light source such that the position is at the focal plane of the focused light. As such, when a position on a substrate is in focus, it is at the focal plane from the focal light. When a position on the surface of a substrate is in focus, it is at an "in-focus-distance". The in-focus-distance usually refers to the absolute distance (in length units e.g. μm) between a position on the surface of an array substrate onto which light is correctly focused and a reference plane of the focusing optical system (e.g. scan lens).

In the methods of the invention, a symmetrical filter is applied to a component signal from a first position of an array substrate. The symmetrically filtered signal is a measurement of the in-focus-distance of the first position.

In general, a symmetrical filter is applied to a component signal generated by a device or sensor that measures an aspect of focus of a light source of the scanner. In some embodiments, the symmetrical filter is applied to a component signal from a device that measures an absolute distance in the scanner, such as a quadrature position encoder and in other embodiments, the symmetrical filter is applied to a component signal generated by focus error measuring device, such as a position sensing detector (PSD). More usually, the symmetrical filter is applied to a component signal that is the summation of component signals generated from a device that measures an absolute distance and a focus error measuring device.

Where a light source is focused upon a position on the surface of a sample the calculated in-focus-distance for the position is sometimes within about +/−5–6 μm of the focal plane of the focused light, normally within about +/−3–5 μm of the focal plane of the focused light, usually within about +/−2–3 μm of the focal plane of the focused light, more usually within about +/−1–2 μm of the focal plane of the focused light and even about +/−0.1–1 μm of the focal plane distance of the focused light.

In many embodiments of the invention, the determined in-focus-distance of the first position of an array is used as an estimate of an in-focus-distance of a second position of a substrate.

Methods of Effecting the Correct Focus of a Light Source onto a Substrate

In general, the calculated in-focus-distance of a first position on the surface of a substrate is used in a method to effect the correct focus of a light source onto a second position a substrate. In most embodiments, these methods involve using a determined in-focus-distance for the first position as an estimate of the actual focal distance for the second position, where the actual focal distance is the physical distance between a position on the surface of a substrate and a fixed reference point of the scanner, such as a light source. The actual focal distance may be measured in any length units, e.g., μm.

In many embodiments, once the in-focus-distance for a first position of a substrate is determined, correct focus of a second position of the substrate is effected, in the case of a fixed focal length scanner, by altering, if necessary, the actual distance between the, second position and a reference position such that the actual focal distance is the same as the in-focus-distance. It is also envisioned that correct focus of a second position may be effected by adjusting a parameter of light focusing device to, e.g., alter the distance of the focal plane of a focused light from the focusing device.

In the context of a scanner, correct focus of a second position of a substrate using a filtered measurement is achieved through a servo control mechanism which adjusts the focus of a focused light based on the determined in-focus-distance for the first position. In general, the servo control mechanism is controlled by a voltage that is proportional to the size of the determined in-focus-distance. As such, the method of the invention may be used in a focus control loop to automatically provide automatic correct focus of a second position of a substrate. In such methods, the determined in-focus-distance for a first position is converted into a voltage, and the voltage is applied to a servo motor that adjusts the actual focal distance of a second position of a substrate as a focused light is approaching the second position.

Focus and servo control loops using voltage are well known in the art. Other control loops (e.g. those using current) for controlling a servo are also known. Servo control may also be effected by a signal proportional to the focus error, where the actual focus error is the calculated distance, expressed in measurement units, e.g., µm, motor step units etc., between the actual focal distance of a position on the surface of an array and the in-focus-distance to the same position.

Usually, the servo motor sets the distance between the second position of a substrate and a fixed reference point (e.g. a light source) such that the distance is within about +/−3–5 µm of the determined in-focus-distance for the first position. However, distances within about +/−3 µm–5 µm, within about 2 µm–3 µm, within about 1 µm–2 µm within about 0.5 µm–1 µm and within about 0.1 µm-0.5 µm of the determined in-focus-distance are also envisioned.

The above methods of effecting correct focus of a light source onto a substrate may be employed in an iterative process, where, as a sample is being scanned, component signals are continuously detected as a moving window, the size of which corresponds to the order of the filter.

Methods of Scanning a Sample

The methods of effecting the correct focus of a focused light onto a substrate, as described above, may be employed in a method of scanning a sample, particularly a biopolymeric array. In scanning a sample, a light, usually a light generated by a laser, is focused onto the surface of the substrate and the surface of the substrate is scanned in a rastered manner, meaning that the focused light travels in a straight line across the surface of the sample several times, each line parallel to the next, and adjacent line scanned after the previous. A scan of a sample is therefore represented by a series of scan lines, each line of which is both parallel to and adjacent to a previously scanned scan line.

In general, the methods of scanning a sample involve automatically focusing a light on the surface of a substrate while the substrate is being scanned. Automatic focus is achieved by determining an in-focus-distance for a first position of the surface, and automatically focusing a light source according to the determined in-focus-distance as the second position is being scanned. As such, the sequence of events achieving correct focus of a second position while scanning a sample are: 1) scanning a first position; 2) symmetrically filtering at least one component signal from the first position to generate an in-focus-distance; and 3) before the scanner scans the second position, effecting correct focus of a light source at the second position using the in-focus-distance of the first position. This process maybe performed automatically using a focus control loop using a, servo motor and, as such, the process may be performed iteratively and in real time during the scanning of a sample, where the focal distance for each position on the surface of a substrate is determined by an in-focus-distance calculated for a previously scanned position. Using this method, each position of an entire substrate may be scanned in focus.

In most embodiments of the invention the first and second positions on the surface of a substrate are at identical or near identical positions in two adjacent scan lines i.e. they are at equal distances from the same end (e.g. the end at the top of a substrate or the left end of a substrate) of adjacent scan lines, where the first position is scanned before the second position. In this embodiment, the in-focus-distance of a first position on the surface of a substrate is estimated using the in-focus-distance of a second position that is situated immediately next to the first position, but on an adjacent scan line. As such, using the methods of the invention, each line of a raster scan is scanned at a focal distance determined by a position on a previously scanned line.

As long as filtering a component signal of a first position is performed before actual scanning of a second position takes place, the timing of filtering and processing a filtered signal of a first position is not important to the process of scanning. As such, the filtering may be performed immediately after scanning the first position, immediately before focusing a light as it approaches the second position, in the "turn around" time, at the end of each scan line etc. Focus adjustment of a scanner to a second position on a sample should be effected immediately before a focused light reaches the second position, ideally after scanning a position immediately before the second position.

In scanning a sample, the accuracy of the focus across a sample is determined by how many times the in-focus-distance is determined in a previous scan line and how many times the focusing of the light source is adjusted while scanning a line. Optimally, the in-focus-distance for every signal (i.e. every pixel) of a scan line is determined, however, in-focus-distances for every 5 or more pixels, 10 or more pixels, or 20 or more pixels or more will generally suffice. Signals from several pixels may also be summed or averaged in determining an in-focus-distance. During the scanning of a line, the light source is optimally focused at a rate equivalent to the number of times an in-focus-distance is determined on the previous line. However, in a standard 25 mm×75 mm microscope slide, a focus adjustment every 10 µm or less, every 20 µm or less, every 50 µm or less, every 100 µm or less or even every 500 µm or 1 mm or less, e.g., 10 mm or less, will generally suffice.

An alternative embodiment of this method includes symmetrically filtering signals from several prior line scans in order to determine an estimated in-focus-distance for a future position.

The methods may also be used with other focus servo control methods such as those utilizing PID or related control algorithms.

For the absolute first position of an array there exits no prior position information to be used as an estimate of the first position. In other words, in our current embodiment for the first line of a scan, there exists no "prior-scan-line" model. Hence, for the first scan line, a conventional feedback focus control loop can be employed. From the second scan line onwards, the "in-focus-distance" of the previous scan line can be used as an estimate of an "in-focus-distance" of the current scan line. Of course, suitably averaged (e.g. weighted average) data from more than one previously scanned line can be used instead of data from just the last previous/closest scan line. Although much of the above methodology has been described above in terms of a particular embodiment, it is not intended that the invention be limited to this embodiment. Modifications within the spirit of the invention will be apparent to those skilled in the art. For example, many different methods for raster scanning a sample, many different variations of symmetrical filters and several different ways of measuring the-in-focus-distance may be employed. The in-focus-distance may also be measured in several ways, for example by distance from a fixed point, by absolute position, or the sum of an absolute distance and an error distance. Also, the automated focus-distance determination routines can be implemented in many different languages, or hardware circuits, in an almost limitless number of ways, using different modular organizations and control logic.

Programming according to the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above described methodology.

A suitable device for scanning a sample employing the above methods is described in the next section.

Optical Scanners

Also provided by the subject invention are biopolymer array optical scanners that are programmed as described above. Any biopolymer optical scanner or device may be provided to include the above programming. Representative optical scanners of interest include those described in U.S. Pat. Nos. 5,585,639; 5,760,951; 5,763,870; 6,084, 991; 6,222,664; 6,284,465; 6,329,196; 6,371,370 and 6,406,849—the disclosures of which are herein incorporated by reference. An exemplary optical scanner as may be used in the present invention is shown in FIG. 1.

Referring now to FIG. 1, an apparatus of the present invention (which may be generally referenced as an array "scanner") is illustrated. A light system provides light from a laser 100 which passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100a, 100b is transmitted through a dichroic beam splitter 154, reflected off fully reflecting mirror 156 and focused onto an array mounted on holder 200, using optical components in beam focuser 160. Light emitted (in particular, fluorescence) at two different wavelengths (e.g., green and red light) from features on the array, in response to the interrogating light, is imaged using the same optics in focuser/scanner 160, and is reflected off mirrors 156 and 154. The two different wavelengths are separated by a further dichroic mirror 158 and are passed to respective detectors 150a and 150b.

More optical components (not shown) may be used between the dichroic and each detector 150a, 150b (such as lenses, pinholes, filters, fibers, etc.) and each detector 150a, 150b may be of various different types (e.g., a photo-multiplier tube (PMT) or a CCD or an avalanche photodiode (APD)). All of the optical components through which light emitted from an array 12 or calibration member 230 in response to the illuminating laser light, passes to detectors 150a, 150b, together with those detectors, form a detection system. This detection system has a fixed focal plane. A scan system causes the illuminating region in the form of a light spot from each laser 100a, 100b, and a detecting region of each detector 150a, 150b (which detecting region will form a pixel in the detected image), to be scanned across multiple regions of an array or array package mounted on holder 200. The scanned regions for an array will include at least the multiple features of the array. In particular the scanning system is typically a line by line scanner, scanning the interrogating light in a line across an array when at the reading position, in a direction of arrow 166, then moving ("transitioning") the interrogating light in a direction into/out of the paper as viewed in FIG. 1 to a position at an end of a next line, and repeating the line scanning and transitioning until the entire array has been scanned.

This scanning feature is accomplished by providing a housing 164 containing mirror 158 and focuser 160, which housing 164 can be moved along a line of pixels (i.e., from left to right or the reverse as viewed in FIG. 3) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The reader of FIG. 1 may further include a reader (not shown) which reads an identifier from an array package. When identifier 40 is in the form of a bar code, that reader may be a suitable bar code reader.

Of course, the movements 166 and 192 may be accomplished by actuating holder 200 or housing 164 alone. Still further, the movement roles described for each element above may be swapped.

A device for measuring signal focus error, e.g. an position sensitive detector 170 is provided to sense any offset between a region of an array when in the reading position, and a determined position of the focal plane of the detection system. The autofocus system includes detector 170, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, a position detector 202 e.g. a quadrature position encoder, also feeding back to the CU measures the absolute position (i.e., relative to the apparatus) of the servo-controlled adjuster 190). As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors.

Controller 180 of the apparatus is connected to receive signals from detectors 150*a*, 150*b* (these different signals being different "channels"), namely a signal which results at each of the multiple detected wavelengths from emitted light for each scanned region of array 12 when at the reading position mounted in holder 200. Controller 180 also receives the signal from autofocus offset detector 170 and absolute servo position detector 202, and provides the control signal to EOM 110, and controls the scan system. Controller 180 contains all the necessary software to symmetrically filter a signal from detectors 170 and 202, and regulate a motorized or servo-controlled adjuster 190 through a control loop. Controller 180 may also analyze, store, and/or output data relating to emitted signals received from detectors 150*a*, 150*b* in a known manner.

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

Controller 180 is suitably programmed to receive signals from autofocus detector 170 and absolute position detector 202 and execute all of the steps required by it during operation of the apparatus, as discussed further above. In general, the controller 180 receives analog or digital position signals for a first position from detectors 170 and 202, filters the signals using a symmetrical filter to determine an in-focus-distance, uses said in-focus-distance to calculate the actual focal distance for a second position of the array, and directs the adjustment of scanner focus immediately before the second point is scanned. Usually, the in-focus-distance of the first position of the array is the same as the actual focal distance for a second position of the array.

In most embodiments of the scanner, the automatic focus of a light onto a position on an array is achieved through a focus control loop, executed by controller 180.

In one mode of operation, an array in a package is typically first exposed to a liquid sample. This liquid sample may be placed directly on the array or introduced into a chamber through a septa in the housing of the array. After a time to allow, for example, hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

The saved results from a sample exposed array, read with focal distances set according to the present invention, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

While it is noted that a scanner that reverses scanning direction at the end of each scan line (i.e a bi-directional scanner) is disclosed, unidirectional scanners also find use with the methods of the invention.

Utility

The subject autofocus biopolymer optical scanners find use in a variety applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143, 854; 5,288,644; 5,324,633; 5,432,049; 5,470,710; 5,492, 806; 5,503,980; 5,510,270; 5,525,464; 5,547,839; 5,580, 732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436, 170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array.

It is further noted that aspects of the invention may be applicable to a variety of optical scanners including those that detect chemiluminescent or electroluminescent labels. The present invention will be applicable to such scanners where powering down the scanner will result in lifetime savings, as exemplified above.

In any case, results from reading an array may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

Kits

Kits for use in connection with the subject invention may also be provided. Such kits preferably include at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In addition to the subject autofocus programming and instructions, the kits may also include one or more reference arrays, e.g., two or more reference arrays for use in testing an optical scanner after software installation.

The following examples are offered by way of illustration and not by any way of limitation.

EXPERIMENTAL

In this example, the methods of the invention are employed in a bi-directional microarray scanner such as model number 2565AA made by Agilent Technologies (Palo Alto Calif.), which scans each adjacent line of a raster scan in an opposite direction. Alternative embodiments in which the methods are employed in a unidirectional scanner are also envisioned.

In scanning a sample, the methodology utilized by the scanner is generally described below.

Since a raster scanner scans back and forth over almost the same surface terrain, a prediction can be made about the in-focus-distance of a point on the surface of an array by adding the measured focus error and the measured absolute position at the corresponding point of a previous line scan. This "prior scan line" model conforms to the following equation:

$$p'_{n+1}(x) = p_n(x) + e_n(x) \qquad \text{(equation 1)},$$

where $p'_{n+1}(x)$ is the predicted absolute position at horizontal scan position x on scan line n+1; $p_n(x)$ is the actual measured position at the same horizontal scan position x on the previous scan line (n); and $e_n(x)$ is the measured focus position error at that point on the previous line (n).

The focus controller of this scanner has no direct information about the horizontal lens position (x), but since it receives a signal from the scanner when the lens first enters the active scan region (to initiate focus control) and the time it leaves the scan region (to maintain position and no longer attempt to control focus), the focus controller may use a timer from the start of the scan region as a proxy for physical distance. Of course, the invention also applies to scanners designed to provide a direct means of determining scan position to the autofocus control system. If N is the number of clocked position measurements made by the focus controller between the time the lens enters the scan region and the time it leaves the scan region, the i'th point is sampled during the scan line n when the lens is at the same x position as it was when the (N+1−i)'th point was pled in the previous scan line. So, for a bi-directional scanner such as Agilent's models G2565AA, G2505A or G2505B, the following equation may be used to describe how a prediction of absolute position can be determined for a position i on line n+1:

$$p'_{n+1}(i) = p_n(N+1-i) + e_n(N+1-i) \qquad \text{(equation 2)}:$$

where i=1 for the first point sampled from the active area of a line scan and i=N for the last point on the active area of the same line scan.

However, such predictions would be no more accurate than direct measurements of focus error on the current scan line, because they are affected by the same noise that affect the measurements of focus error ($e_n$) and absolute position ($p_n$)

Inclusion of a symmetrical low-pass or bandpass digital filter can greatly attenuate such noise, and therefore improves the accuracy of the prediction considerably.

The output of equation (2) is subjected to a symmetrical low-pass or bandpass digital filter (to result in a predicted in-focus-distance), improving the accuracy of a prediction considerably. The symmetrically filtered absolute position predictions are described by the following equation:

$$f_{n+1}(i) = \sum_{j=i-k}^{i+k} s(j) p'_{n+1}(j) \quad \text{(equation 3)}$$

where $f_{n+1}(i)$ is the filtered output of the i'th position on the (n+1)th row, s(j)'s are coefficients of a filter with an order of 2k+1. As such, the filtered output is based on k past and k future values of the sum of the quadrature encoder position signal and the focus error signal determined using PSD. The filter is zero-phased and hence the signal f is in phase with the predicted position signal p'.

The controller then controls the absolute position of a substrate, in this case a biopolymeric array, to minimize the difference between the actual measured position $p_{n+1}(i)$ (i.e. the absolute focal distance) and the filtered prediction $f_{n+1}(i)$ (i.e. the in-focus-distance).

Figure 2:
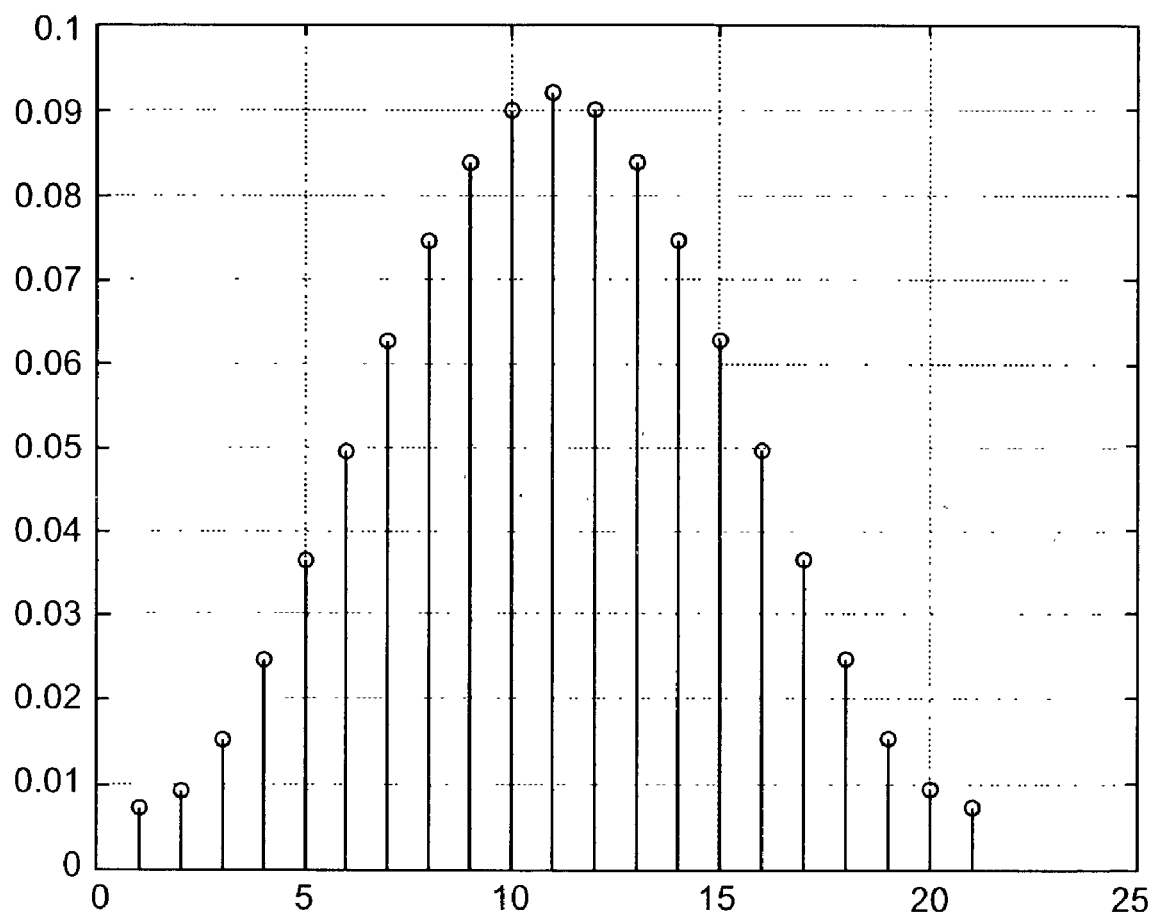
FIG. 2 diagrammatically shows the coefficients of equation 3 for a $21^{st}$ order filter.

Although implementing and designing symmetrical filters is well within the skill of an artisan, one example of the coefficients of a $21^{st}$ order filter is provided (FIG. 2). When a zero-phase or symmetrical filter is used, then the $11^{th}$ signal is filtered using data from positions 1–10 (previously scanned positions), position 11, and positions 12–21 (scanned after position 11). Weightings for each position are given on the Y axis of this graph.

Figure 3:
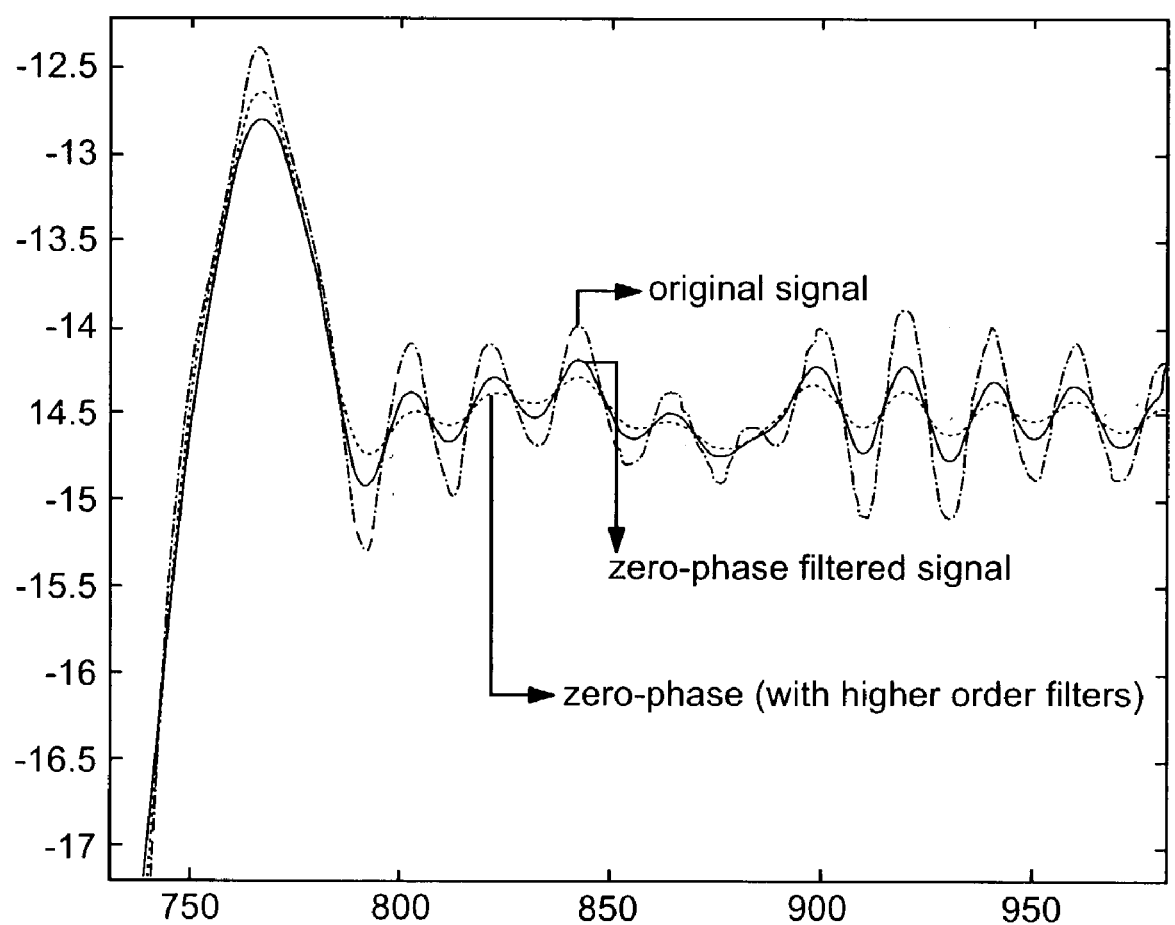
FIG. 3 is a graph of signal magnitude versus time with an unfiltered signal, a signal filtered with a zero-phase filter, and a signal filtered with a higher order zero phase filter.

Exemplary results of the invention are provided in FIG. 3, where signal magnitude x-axis) is plotted against time (y-axis) for an unfiltered signal ("original signal"), a signal filtered with a moderate order symmetrical filter ("zero phase filtered signal") and a signal filtered with a higher order symmetrical filter ("zero phase with higher order filter"). A marked reduction in the amplitude of high frequency signal is observed when a symmetrical filter is used.

Of course, these methods may be adapted to scanners that scan vertically (i.e. in a raster of "up-and-down" scan lines, as well as scanners that scan horizontally.

It is evident from the above results and discussion that the subject invention provides an important new means for scanning a substrate. Specifically, the subject invention provides a system for maintaining correct focus of a light source while scanning a biopolymeric array. As such, the subject methods and systems find use in a variety of different applications, including research, diagnostic and other applications. Accordingly, the present invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of determining an in-focus-distance for a first position on a surface of a biopolymeric array, said method comprising:
    detecting a signal from said first position of said surface; and
    filtering said signal using a symmetrical filter to determine said in-focus-distance for said first position.

2. The method of claim 1, wherein said in-focus-distance is used as an estimate of an in-focus-distance of a second position of said biopolymeric array.

3. The method of claim 1, whereby said symmetrical filter utilizes secondary signals from at least one side-position on each side of said first position to filter said signal from said first position.

4. The method of claim 3, wherein said first position and said side-positions on each side of said first position are located on a single scan line.

5. The method of claim 4, wherein said side-positions are arranged in pairs of side-positions that are equidistant from the first position.

6. The method of claim 1, wherein said symmetrical filter is a zero phase filter.

7. The method of claim 1, wherein said signal is the sum of a first component signal of an absolute position measuring device and a second component signal of a focus error measuring device.

8. The method of claim 7, wherein said absolute position measuring device is a quadrature position encoder.

9. The method of claim 7, wherein said focus error measuring device is a position sensitive detector.

10. The method of claim 1, wherein said in-focus-distance is within about +/−3–5μm of the focal plane of a focused light.

11. The method of claim 1, wherein said filtering step removes noise from said signal to allow an accurate determination of said in-focus-distance.

12. The method of claim 11, wherein said noise is at a frequency of approximately 150–1000 Hz.

13. The method of claim 1, wherein said signal is a fluorescent signal.

14. The method of claim 1, wherein the biopolymeric array is an array of polynucleotides or polypeptides.

15. A method of focusing a light source onto a second position on a surface of a biopolymeric array, the method comprising:
    (a) predicting an in-focus-distance for a second position on a surface of said biopolymeric array using the method of claim 2; and
    (b) focusing said light said onto said second position using said predicted in-focus-distance.

16. The method of claim 15, wherein said focusing step is automatic.

17. The method of claim 16, wherein said focusing step is performed using a focus control loop.

18. The method of claim 15, wherein said first position and said second position are on adjacent scan lines.

19. The method of claim 15, further comprising the step of scanning said second position at said in-focus-distance.

20. The method of claim 19, wherein said method is employed in a method of maintaining focus of a light source while scanning a biopolymeric array using a scanner system.

21. The method of claim 15, wherein said scanner is a bidirectional line scanner.

22. A computer-readable medium encoding instructions to direct a machine to perform the method of claim 1.

23. A biopolymer array scanner comprising a computer-readable medium according to claim 22.

24. A method of assaying a sample, said method comprising:
(a) contacting said sample with a biopolymeric array of two or more biopolymer ligands immobilized on a surface of a solid support; and
(b) reading said array with a biopolymer array scanner according to claim 23 to obtain a result.

25. The method according to claim 24, wherein said reading step (b) includes:
(i) symmetrically filtering a detected signal from a first position of a scanned line to determine an estimated in-focus-distance for a second position; and
(ii) automatically focusing a laser of the scanner at said second position using said estimated in-focus-distance.

26. The method according to claim 25, wherein said biopolymer array is chosen from a polypeptide array and a nucleic acid array.

27. A method comprising transmitting a result obtained from a method of claim 25, from a first location to a second location.

28. The method of claim 27, where said second location is a remote location.

29. A method comprising receiving data representing said result of a scan obtained by the method of claim 25.

30. A kit for use in a biopolymer array optical scanner, said kit comprising:
(a) a computer-readable medium according to claim 22; and
(b) instructions for operating said scanner according to said programming.

31. The kit according to claim 30, wherein said kit further includes at least one reference array.

32. The kit according to claims 31, wherein the kit further includes instructions for installing the encoded instructions.

* * * * *

UNITED STATES PATENT AND TRADEMARK OFFICE
CERTIFICATE OF CORRECTION

| | | |
|---|---|---|
| PATENT NO. | : 7,067,783 B2 | Page 1 of 1 |
| APPLICATION NO. | : 10/261359 | |
| DATED | : June 27, 2006 | |
| INVENTOR(S) | : Curry et al. | |

It is certified that error appears in the above-identified patent and that said Letters Patent is hereby corrected as shown below:

On the Title page, Item (56), under "U.S. Patent Documents", in column 2, line 3, delete "Fodore t al." and insert -- Fodor et al. --, therefor.

On the Title page, Item (56), under "U.S. Patent Documents", in column 2, line 6, delete "Sadlere et al." and insert -- Sadler et al. --, therefor.

In column 22, line 21, in Claim 32, delete "claims 31," and insert -- claim 31, --, therefor.

Signed and Sealed this

Twenty-eighth Day of November, 2006

JON W. DUDAS
*Director of the United States Patent and Trademark Office*